(12) United States Patent
Salisbury et al.

(10) Patent No.: US 8,519,182 B2
(45) Date of Patent: Aug. 27, 2013

(54) ACETIC ACID PRODUCTION PROCESS

(75) Inventors: Brian A. Salisbury, Oxford, PA (US); Noel C. Hallinan, Loveland, OH (US)

(73) Assignee: Lyondell Chemical Technology, L.P., Houston, TX (US)

( * ) Notice: Subject to any disclaimer, the term of this patent is extended or adjusted under 35 U.S.C. 154(b) by 80 days.

(21) Appl. No.: 12/906,575

(22) Filed: Oct. 18, 2010

(65) Prior Publication Data

US 2012/0095259 A1  Apr. 19, 2012

(51) Int. Cl.
*C07C 51/12* (2006.01)

(52) U.S. Cl.
USPC .......................................................... 562/519

(58) Field of Classification Search
None
See application file for complete search history.

(56) References Cited

U.S. PATENT DOCUMENTS

| | | | |
|---|---|---|---|
| 3,743,607 A | 7/1973 | Sennewald et al. | |
| 5,817,869 A | 10/1998 | Hinnenkamp et al. | |
| 5,932,764 A | 8/1999 | Morris et al. | |
| 6,022,823 A | 2/2000 | Augustine et al. | |
| 6,046,809 A * | 4/2000 | deGroot et al. | 356/337 |
| 6,103,934 A * | 8/2000 | Hallinan et al. | 562/517 |
| 6,255,527 B1 * | 7/2001 | Muskett | 562/519 |
| 6,362,366 B1 * | 3/2002 | Hallinan et al. | 562/517 |
| 6,420,595 B1 | 7/2002 | Hallinan et al. | |
| 6,552,221 B1 * | 4/2003 | Hallinan et al. | 562/519 |
| 6,677,480 B2 * | 1/2004 | Huckman et al. | 562/519 |
| 7,476,761 B2 | 1/2009 | Kojima | |
| 7,505,127 B2 | 3/2009 | Marrow et al. | |
| 2005/0154228 A1 * | 7/2005 | Nakajima et al. | 562/519 |
| 2012/0130119 A1 | 5/2012 | Salisbury et al. | |

FOREIGN PATENT DOCUMENTS

WO  WO 2010/014583 A1  2/2010

OTHER PUBLICATIONS

"Acetic Acid" in Ullmann's Encyclopedia of Industrial Chemistry Hosea Cheung, Robin S. Tanke and G. Paul Torrence, 1999-2012 John Wiley & Sons, Inc. pp. 209-237.*

J. M. Tedesco et al., "Calibration of dispersive Raman Process Analyzers," The Society of Photo-Optical Instrumentation Engineers, vol. 3537, pp. 200-212, 1999.*

S.E. Nave "Rugged Fiber Optic Probes and Sampling Systems for Remote Chemical Analysis Via the Raman Technique," ISA, Paper #96-042, pp. 453-467, 1996.*

M.J. Pelletier et al.; "Optical fibers enable Raman instruments to analyze industrial process problems quickly and accurately," Raman Spectroscopy-Keeps Industry Under Control, Reprint: Photonics Spectra, 4 pgs., Oct. 1997.*

"Acetic Acid" in Ullmann's Encyclopedia of Industrial Chemistry Hosea Cheung, Robin S. Tanke and G. Paul Torrence, 1999-2005 John Wiley & Sons, Inc. pp. 1-30.*

Sunley G J et al: "High productivity 1-12 methanol carbonylation catalysis using iridium. The Cativa process for the manufacture of acetic acid", Catalysis Today, Amsterdam, NL, vol. 58, No. 4, Jan. 1, 2000, pp. 293-307, XP002264805.

Ian Lewis: "14th NIChE Conference on Micro-Reactor Technologies", Micro-Reactor Technologies: A Critical Tool for Process Optimization and Intensification, Sep. 22, 2009, XP55012283, Retrieved from the Internet: URL:http://www.ccrhq.org/14th-niche-conference-micro-reactor-technologies>.

Denis Forster: "On the mechanism of a rhodium-complex-catalyzed carbonylation of methanol to acetic acid", Journal of the American Chemical Society, vol. 98, No. 3, Feb. 1, 1976, pp. 846-848, XP55012166.

H Chung: "Feasibility of monitoring acetic acid process using near-infrared spectroscopy", Vibrational Spectroscopy, vol. 31, No. 1, Jan. 15, 2003, pp. 125-131, XP55012187.

Selena E. Richards et al.: "A Novel Approach to the Quantification of Industrial Mixtures from the Vinyl Acetate Monomer (VAM) process using Near Infrared Spectroscopic Data and a Quantitative Self Modeling Curve Resolution (SMCR) Methodology", Chemmomimetrics and Intelligent Laboratory Systems, vol. 94, pp. 9-18, 2008.

David D. Kragetn et al.: "A Spectroscopic Study of the Homogeneous Catalytic Conversion of Ethylene to Vinyl Acetate by Palladium Acetate," Inorganic Chemistry, vol. 38, No. 2, Jan. 1, 1999, pp. 331-339, XP55025086, ISSN:0020-1669, DOI: 10.1021/ic980399g, the whole document.

Talat Oxpozn et al.: "Monitoring of the Polymerization of Vinylacetate by Near IR FR Raman Spectroscopy", Spectrochimica Acts, vol. 53, No. 1, 1997, pp. 1-7, XPoo2674945, the whole document.

\* cited by examiner

*Primary Examiner* — Karl J Puttlitz

(57) ABSTRACT

Disclosed is a method for controlling an acetic acid production process. The method comprises: (i) reacting methanol and carbon monoxide in the presence of a carbonylation catalyst, a catalyst stabilizer, methyl iodide, water, and methyl acetate to produce a reactor mixture which comprises the catalyst, the catalyst stabilizer, methanol, carbon monoxide, carbon dioxide, methyl iodide, methyl acetate, water, and acetic acid; (ii) measuring the concentration of a component of the reactor mixture by Raman spectroscopic analysis; and (iii) adjusting the component concentration in the reactor mixture in response to the measured concentration. The method of the invention is particularly useful for measuring and controlling the concentration of carbon monoxide in the reactor liquid mixture.

8 Claims, No Drawings

ACETIC ACID PRODUCTION PROCESS

FIELD OF THE INVENTION

The invention relates to the preparation of acetic acid. More particularly, the invention relates to a method for controlling the acetic acid production process by Raman spectroscopy.

BACKGROUND OF THE INVENTION

Acetic acid is commercially produced by methanol carbonylation. Prior to 1970, acetic acid was made using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem associated with the original Monsanto process is that a large amount of water (about 14%) is needed to produce hydrogen in the reactor via the water-gas shift reaction ($CO+H_2O \rightleftharpoons CO_2+H_2$). Water and hydrogen are needed to react with precipitated Rh(III) and inactive $[Rh_4(CO)_2]$ to regenerate the active Rh(I) catalyst. This large amount of water increases the amount of hydrogen iodide, which is highly corrosive and leads to engineering problems. Further, removing a large amount of water from the acetic acid product is costly.

In the late '70s, Celanese modified the carbonylation process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the early '90s, Millennium Petrochemicals developed a new rhodium carbonylation catalyst system that does not use iodide salt. The catalyst system uses a pentavalent Group VA oxide such as triphenylphosphine oxide as a catalyst stabilizer. The Millennium catalyst system not only reduces the amount of water needed but also increases the carbonylation rate and acetic acid yield. See U.S. Pat. No. 5,817,869.

One important issue in the low-water carbonylation process is to measure and control the concentration of carbon monoxide in the reactor liquid so that a sufficient amount of hydrogen is generated to allow the reduction of the Rh(III) to active Rh(I) catalyst. Direct measurement of the carbon monoxide concentration in the reactor liquid is a challenge and no direct analytical method has been developed in the art. U.S. Pat. No. 7,476,761 teaches an indirect measurement. According to the '761 patent, the reactor liquid is withdrawn from the reactor and flashed into a gas mixture and a liquid. The gas mixture contains carbon monoxide and other volatile components. The gas mixture passes through a control apparatus where the carbon monoxide is measured. The carbon monoxide concentration in the reactor liquid is then estimated or calculated based on the carbon monoxide concentration in the gas mixture.

U.S. Pat. No. 6,552,221 also teaches process control for acetic acid manufacture. According to the '221 patent, samples are collected from columns and/or transfer lines downstream of a reactor vessel, and the concentration of one or more components in the sample is measured by an infrared analyzer. The concentration measurements are then used to make adjustments in the concentration of components in the reaction system, directly or indirectly, such as by adjusting the temperature profile in a particular column, the flow rate of solution into or out of a column, the vent gas rate out of the reactor or a column, or the addition or extraction of a component to or from the solution. The components measured include water, acetic acid, methyl acetate, methyl iodide, aldehydes, hydrocarbons, propionic acid, and hydrogen iodide. Similarly, U.S. Pat. No. 6,362,366 teaches an online method to measure components in the reactor mixture.

New methods for measuring carbon monoxide and other components in the reactor liquid of the methanol carbonylation are needed. Ideally, the method can directly measure the carbon monoxide concentration in the reactor liquid.

SUMMARY OF THE INVENTION

The invention relates to a method for controlling an acetic acid production process. The method comprises: (i) reacting methanol and carbon monoxide in the presence of a carbonylation catalyst, a catalyst stabilizer, methyl iodide, water, and methyl acetate to produce a reactor mixture which comprises the catalyst, the catalyst stabilizer, methanol, carbon monoxide, carbon dioxide, methyl iodide, methyl acetate, water, and acetic acid; (ii) measuring the concentration of a component of the reactor mixture by Raman spectroscopic analysis; and (iii) adjusting the component concentration in the reactor mixture in response to the measured concentration. The method of the invention is particularly useful for measuring and controlling the concentration of carbon monoxide in the reactor liquid mixture. The carbon monoxide concentration in the reactor mixture liquid determines the catalyst stability and reactivity. Traditionally, the carbon monoxide concentration in the reactor mixture liquid is measured indirectly. The invention provides a direct measurement of the carbon monoxide concentration in the reactor mixture liquid which improves the process control of the methanol carbonylation.

DETAILED DESCRIPTION OF THE INVENTION

The invention relates to a method for controlling a methanol carbonylation process by Raman spectroscopy. The carbonylation reaction is usually performed in the presence of a carbonylation catalyst and a catalyst stabilizer. Suitable carbonylation catalysts include those known in the acetic acid industry. Examples of suitable carbonylation catalysts include rhodium catalysts and iridium catalysts. Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_3$, the like, and mixtures thereof.

Suitable iridium catalysts are taught, for example, by U.S. Pat. No. 5,932,764. Suitable iridium catalysts include indium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-$ $H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(Ac)_3$, $[Ir_3O(OAc)_6(H_2O)_3][OAc]$, and H₂[IrCl₆]. Preferably, the iridium compounds are selected from the group consisting of acetates, oxalates, acetoacetates, the like, and mixtures thereof. More preferably, the iridium compounds are acetates. The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are chloride-free such as acetates.

Preferably, the reaction is performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817, 869. Phosphine oxides are more preferred. Triphenylphosphine oxides are most preferred.

The carbonylation reaction is performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

Preferably, the reaction is performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the acetic reactor and then reacts with carbon monoxide and water to give acetic acid and regenerate the hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including acetaldehyde. The liquid fraction is preferably recycled to the carbonylation reactor. The vapor fraction is then passed to a distillation column.

The distillation column, the so called "light ends distillation," separates an overhead comprising methyl iodide, water, methanol, methyl acetate, and acetaldehyde from an acetic acid stream comprising acetic acid, a small amount of water, and heavy impurities such as propionic acid. The acetic acid stream may be passed to a drying column to remove water and then be subjected to the so called "heavy ends distillation" to remove the heavy impurities.

The overhead from the light-ends distillation preferably comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of alkanes, and about 2 wt % or less of acetaldehyde based on the total weight of the overhead.

The overhead is condensed and separated in a decanter to a light, aqueous phase and a heavy, organic phase. The heavy, organic phase comprises methyl iodide and the acetaldehyde. The light, aqueous phase comprises water, acetic acid, and methyl acetate. The aqueous phase is preferably recycled to the reactor or to the light ends distillation.

The method of the invention comprises measuring the component concentration of the reactor mixture by Raman spectroscopy. Raman spectroscopy is known, for instance, see U.S. Pat. No. 7,505,127. The Raman shift occurs when light impinges upon a molecule and interacts with the electron cloud and the bonds of that molecule. A photon excites the molecule from the ground state to a virtual energy state. When the molecule relaxes, it emits a photon and it returns to a different rotational or vibrational state. The difference in energy between the original state and this new state leads to a shift in the emitted photon's frequency away from the excitation wavelength. Raman spectra are typically shown as plots of intensity (arbitrary units) versus Raman shift. Raman shifts are typically expressed in wavenumbers, which have units of inverse length. Most commonly, the units chosen for expressing wavenumber in Raman spectra is inverse centimeters ($cm^{-1}$).

The instrumentation used to collect and process Raman data includes a Raman spectrometer system, a transmittance system, a control loop, and a processor. The Raman spectrometer system comprises a Raman spectrometer, the principal components of which are light source, a monochromator, and a detector. The light source delivers excitation radiation to the probe. Scattered radiation is collected, filtered of Raleigh scattered light, and dispersed via a monochromator. The dispersed Raman scattered light is then imaged onto a detector and subsequently processed within the processor.

Typically, the light source is a visible laser, such as a frequency-doubled Nd:YAG laser (532 nm), a helium-neon laser (633 nm), or a solid-state diode laser (such as 785 nm).

The laser can be pulsed or continuous wave (CW), polarized as desired or randomly polarized, and preferably single-mode. Typical excitation lasers will have 100 to 400 mW power (CW), although lower or higher power can be used as desired. Light sources other than lasers can be used, and wavelengths and laser types and parameters other than those listed above can also be used.

The excitation radiation can be delivered to the probe, and the scattered radiation collected from the probe by any convenient means known in the art, such as conventional beam manipulation optics or fiber optic cables generally designated. For an online process measurement, it is particularly convenient to deliver the excitation radiation and collect the scattered radiation through fiber optic cables. It is a particular advantage of Raman spectroscopy that the excitation radiation typically used is readily manipulated fiber optically, and thus the excitation source can be positioned remotely from the sampling region.

The scattered radiation is collected and dispersed by any convenient means known in the art, such as a fiber optic probe. The collected scattered radiation is filtered to remove Raleigh scattering and then frequency (wavelength) dispersed using a suitable dispersive element, such as a blazed grating or a holographic grating, or interferometrically (e.g., using Fourier transforms). The grating can be fixed or scanned, depending upon the type of detector used. The monochromator can be any such dispersive element, along with associated filters and beam manipulation optics.

The dispersed Raman scattering is imaged onto a detector. Typical detectors include array detectors generally used with fixed-dispersive monochromators, such as diode arrays or charge coupled devices (CCDs), or single element detectors generally used with scanning-dispersive monochromators or FT-based spectrometers, such as lead sulfide detectors and indium-gallium-arsenide detectors. In the case of array detectors, the detector is calibrated such that the frequency (wavelength) corresponding to each detector element is known. The detector response is delivered to the processor that generates a set of frequency shift, intensity (x,y) data points which constitute the Raman spectrum.

The scattered radiation of the carbonylation reaction mixture may be collected by a probe in a variety of locations within the methanol carbonylation system, but preferably in the carbonylation reactor mixture liquid. The probe can directly contact with the reactor liquid. Alternatively, the probe does not contact with the reactor mixture liquid. The probe delivers the excitation radiation from the light source to the reactor mixture liquid, collects the scattered radiation, and delivers the scattered radiation to the monochromator through the transmittance system.

Many components of the reactor mixture can be measured by Raman spectroscopy, including triphenylphosphine oxide, carbon monoxide, methanol, methyl iodide, methyl acetate, carbon dioxide, acetic acid, water, etc. One advantage of the invention is that the measurement can be performed online, because the scattered radiation can be readily delivered through the transmittance system to a remote location. Another advantage of the invention is that the carbon monoxide concentration in the reactor liquid can be directly measured because carbon monoxide exhibits a strong Raman shift under the carbonylation reaction conditions.

The method of the invention comprises adjusting the conditions in the reactor or in any subsequent step of the acetic acid production process in response to the measured concentration of the components to achieve a proper concentration of the component in the reactor mixture. High methyl acetate concentration in the reactor mixture indicates that the feed rate of methyl acetate is too high or the conversion rate of methyl acetate to acetic acid is too low. In this case, the methyl acetate feed rate can be reduced or the carbonylation reaction temperature can be increased to boost the conversion of methyl acetate to acetic acid. More importantly, the carbon monoxide concentration in the liquid phase of the carbonylation reactor must be controlled in a proper range so that the water-gas shift reaction can produce a sufficient amount of hydrogen to keep the rhodium catalyst reactive. Preferably, the carbon monoxide concentration in the liquid phase is controlled within the range of 0.5 mmol/L to 50 mmol/L, preferably from 1 mmol/L to 25 mmol/L, and most preferably from 2 mmol/L to 20 mmol/L. If the carbon monoxide concentration is too low or too high, its feed rate can be adjusted accordingly.

The following example merely illustrates the invention. Those skilled in the art will recognize many variations that are within the spirit of the invention and scope of the claims.

EXAMPLE

To a 300 mL autoclave, outfitted with a magnetically driven stirrer, is added a solution (200 mL) which contains various components including methyl acetate, methyl iodide, triphenylphosphine oxide, water, acetic acid, carbon monoxide, and carbon dioxide. To identify the Raman shifts and intensity of each component, a number of experiments (normally 8 runs) are performed in which the concentration of said component varies while the concentrations of other components remain essentially constant or under such conditions that the other components will not interfere with the measurement of said component. The reactor mixture flows to a Raman sample cell. The sample cell is made from Hastalloy B2 and is available from Harrick Scientific Company. It is equipped with ⅛ inch swagelok fittings and with Raman grade, 13 mm diameter sapphire windows, and it is connected to an outlet line of the reactor. A CCD Kaiser Optic RXN1-785 Raman spectrometer equipped with an MR-Probe-785 non-contact probe is used for data collection. The reactor contents are heated to 175° C. and pressurized with 400 psig of carbon monoxide. An aliquot is blocked into the heated sample cell where a Raman spectrum is collected at the reactor temperature and pressure. Table 1 lists the Raman shifts of the components.

It is surprisingly observed that CO has a clearly observed and fully resolved Raman shift in the reactor solution while it is essentially not measurable by FTIR. The measured Raman shifts are applied to a carbonylation reaction control. The concentrations determined by calibration models developed by Raman spectroscopic analysis match well with the actual concentrations of the components in the reactor.

TABLE 1

Raman Shifts at 785 nm Laser Wavelength of Carbonylation Reaction Mixture at 175° C. and 400 psig of Carbon Monoxide

| Component | Raman Shift, cm−1 |
|---|---|
| Methyl Acetate | 640, 846 |
| Methyl Iodide | 526 |
| Triphenylphosphine Oxide | 250, 690, 1000, 1170, 1580 |
| Water | 1700, 3480 |
| Acetic Acid | 620, 890, 1675, 2900 |
| Carbon Monoxide | 2145 |
| Carbon Dioxide | 1276 |

We claim:

1. A method for controlling an acetic acid production process, comprising:
   (i) reacting a first concentration of methanol and a first concentration of carbon monoxide in the liquid phase in the presence of:
      a first concentration of a rhodium carbonylation catalyst,
      a first concentration of a catalyst stabilizer,
      a first concentration of methyl iodide,
      a first concentration of water, and
      a first concentration of methyl acetate
      to produce a first reactor mixture which comprises a component selected from the following group:
      the carbonylation rhodium catalyst,
      the catalyst stabilizer,
      methanol,
      carbon monoxide,
      carbon dioxide,
      methyl iodide,
      methyl acetate,
      water, and
      a first concentration of acetic acid;
      wherein the reacting step further comprises the step of: generating hydrogen wherein the hydrogen maintains the activity of the carbonylation rhodium catalyst
   (ii) measuring the first concentration of carbon monoxide by Raman spectroscopic analysis; and
   (iii) adjusting the first concentration of carbon monoxide thereby creating a second concentration of carbon monoxide wherein the second concentration of carbon monoxide is sufficient to produce a second concentration of acetic acid, and wherein the second concentration of acetic acid is greater than the first concentration of acetic acid.

2. The method of claim 1, wherein the second concentration of carbon monoxide is within the range of 0.5 mmol/L to 50 mmol/L.

3. The method of claim 1, wherein the second concentration of carbon monoxide is within the range of 1 mmol/L, to 25 mmol/L.

4. The method of claim 1, wherein the catalyst stabilizer is selected from the group consisting of pentavalent Group VA oxides, metal iodide salts, and mixtures thereof.

5. The method of claim 4, wherein the catalyst stabilizer is a phosphine oxide.

6. The method of claim 5, wherein the catalyst stabilizer is triphenylphosphine oxide.

7. The method of claim 4, wherein the catalyst stabilizer is an alkali halide.

8. The method of claim 7, wherein the catalyst stabilizer is lithium iodide.

* * * * *